US012800449B2

(12) United States Patent
Liu et al.

(10) Patent No.: US 12,800,449 B2
(45) Date of Patent: Nov. 17, 2026

(54) AUTOMATIC TRANSPARENT SOIL PREPARATION BOX

(71) Applicant: Institute for Smart City of Chongqing University in Liyang, Liyang (CN)

(72) Inventors: Hanlong Liu, Liyang (CN); Hang Zhou, Liyang (CN); Longyong Tong, Liyang (CN); Ronglin Chen, Liyang (CN); Xuanming Ding, Liyang (CN)

(73) Assignee: Institute for Smart City of Chongqing University in Liyang, Liyang (CN)

( * ) Notice: Subject to any disclaimer, the term of this patent is extended or adjusted under 35 U.S.C. 154(b) by 539 days.

(21) Appl. No.: 18/477,255

(22) Filed: Sep. 28, 2023

(65) Prior Publication Data

US 2025/0110026 A1 Apr. 3, 2025

(51) Int. Cl.
*G01N 1/28* (2006.01)
*G01N 21/41* (2006.01)
(Continued)

(52) U.S. Cl.
CPC ............. *G01N 1/286* (2013.01); *G01N 21/41* (2013.01); *G01N 33/24* (2013.01); *G01N 2035/00207* (2013.01)

(58) Field of Classification Search
CPC ............ G01N 33/24; G01N 1/28; G01N 1/38; G01N 21/84; G01N 3/068; G01N 3/02; G01N 3/08; G01N 1/42; G01N 1/2806; G01N 33/227; G01N 15/08; G01N 13/04; G01N 2203/0019; G01N 2203/0682; G01N 15/0806; G01N 3/12; G01N 3/24; G01N 15/0826; G01N 13/00; G01N 2203/0647;
(Continued)

(56) References Cited

U.S. PATENT DOCUMENTS 7,461,566 B2 * 12/2008 Brone ...................... G01N 1/20 73/863.21
8,144,319 B2 * 3/2012 Preiner .................. G01N 33/24 356/244
(Continued)

FOREIGN PATENT DOCUMENTS

BR 112020006616 A2 * 10/2020 ............. G01N 33/24
CN 106841111 A * 6/2017 ............. G01N 21/41
(Continued)

*Primary Examiner* — Michael P Stafira
(74) *Attorney, Agent, or Firm* — Westbridge IP LLC

(57) ABSTRACT

An automatic transparent soil preparation box includes an AB liquid mixing module, a refractive index measurement module and a solid particle spreading module which are arranged in a box body. The AB liquid mixing module is configured to inject A/B liquid into a model tank and stir and mix the A/B liquid; the refractive index measurement module is able to suck an AB mixture sample from the model tank and measure a refractive index of the AB mixture sample; the solid particle spreading module is configured to spread solid particles into the model tank and stir and mix the solid particles and an AB mixture. The preparation box integrates functional modules such as liquid mixing, refractive index measurement and solid particle spreading into the preparation box, the preparation process is basically fully automated, the test personnel mainly focus on a test, thereby improving the test efficiency.

13 Claims, 6 Drawing Sheets

(51) Int. Cl.
*G01N 33/24* (2006.01)
*G01N 35/00* (2006.01)

(58) Field of Classification Search
CPC ............ G01N 2203/0003; G01N 1/36; G01N 1/286; G01N 2203/0075; G01N 2203/0641; G01N 21/01; G01N 2013/003; G01N 2203/0676; G01N 15/082; G01N 2203/0025; G01N 1/08; G01N 3/06; G01N 2203/0017; G01N 2203/0048; G01N 33/246; G01N 15/088; G01N 2203/0256; G01N 23/046; G01N 2015/0003; G01N 33/383; G01N 11/00; G01N 15/00; G01N 19/00; G01N 2015/0846; G01N 21/41; G01N 21/85; G01N 3/04; G01N 2001/366; G01N 2203/0033; G01N 3/00; G01N 2011/008; G01N 3/10; G01N 3/14; G01N 3/567; G01N 33/245; G01N 1/04; G01N 1/40; G01N 19/02; G01N 21/03; G01N 21/64; G01N 33/00; G01N 1/34; G01N 2021/8466; G01N 2203/0005; G01N 25/14; G01N 33/0098; G01N 1/44; G01N 17/006; G01N 17/02; G01N 17/04; G01N 2021/0112; G01N 21/253; G01N 21/6452; G01N 21/88; G01N 2203/0026; G01N 2203/0037; G01N 2203/0066; G01N 2203/0087; G01N 2203/0226; G01N 2203/0228; G01N 2203/0284; G01N 2203/0298; G01N 25/20; G01N 27/00; G01N 3/22; G01N 3/32; G01N 5/00; G01N 15/06; G01N 2015/0034; G01N 2021/8411; G01N 21/76; G01N 21/90; G01N 21/9045; G01N 21/93; G01N 21/958; G01N 2203/0044; G01N 2203/0423; G01N 27/041; G01N 3/064; G01N 3/16; G01N 33/18; G01N 5/04; G01N 1/2294; G01N 1/31; G01N 1/4077; G01N 15/02; G01N 17/00; G01N 19/04; G01N 2001/2866; G01N 2001/2873; G01N 2001/364; G01N 2001/4061; G01N 2015/0813; G01N 2021/0106; G01N 2021/8405; G01N 2021/8887; G01N 2035/00188; G01N 21/05; G01N 21/35; G01N 21/3504; G01N 21/3563; G01N 21/359; G01N 21/4133; G01N 21/6458; G01N 21/658; G01N 21/763; G01N 21/8851; G01N 2201/06113; G01N 2201/102; G01N 2201/12; G01N 2203/0067; G01N 2203/0071; G01N 2203/023; G01N 2203/0246; G01N 2203/04; G01N 2203/06; G01N 2223/307; G01N 2223/64; G01N 23/2251; G01N 25/00; G01N 2500/04; G01N 29/07; G01N 3/066; G01N 3/30; G01N 3/307; G01N 3/38; G01N 31/22; G01N 33/0004; G01N 1/10; G01N 1/20; G01N 1/30; G01N 1/4055; G01N 15/0272; G01N 15/075; G01N 15/1436; G01N 15/1456; G01N 15/1468; G01N 2001/1025; G01N 2001/386; G01N 2001/4083; G01N 2001/4088; G01N 2015/0053; G01N 2021/1765; G01N 2021/6471; G01N 2021/855; G01N 2021/8592; G01N 2035/00207; G01N 2035/00475; G01N 2035/00495; G01N 2035/00514; G01N 2035/00534; G01N 21/25; G01N 21/251; G01N 21/255; G01N 21/293; G01N 21/55; G01N 21/643; G01N 21/65; G01N 21/78; G01N 2203/0032; G01N 2203/005; G01N 2203/0053; G01N 2203/0208; G01N 2203/0218; G01N 2203/0222; G01N 2203/0236; G01N 2203/0252; G01N 23/2202; G01N 25/04; G01N 25/18; G01N 27/04; G01N 27/22; G01N 27/226; G01N 27/4161; G01N 3/18; G01N 3/58; G01N 31/02; G01N 33/0031; G01N 33/0037; G01N 33/004; G01N 33/0073; G01N 33/10; G01N 33/1866; G01N 33/5008; G01N 33/502; G01N 33/5044; G01N 33/5076; G01N 33/5088; G01N 33/5308; G01N 33/6872; G01N 35/00; G01N 35/00584; G01N 35/0099; G01N 35/028; G01N 35/08; G01N 35/1004; G01N 35/1072; G01N 35/1095

See application file for complete search history.

(56) References Cited

U.S. PATENT DOCUMENTS

| | | | | | |
|---|---|---|---|---|---|
| 8,325,336 | B2 * | 12/2012 | Preiner | G01N 21/33 356/244 |
| 11,632,914 | B2 * | 4/2023 | Choi | A01C 1/04 47/60 |
| 2023/0417657 | A1 * | 12/2023 | Oeguen | G01J 3/42 |

FOREIGN PATENT DOCUMENTS

| | | | | | |
|---|---|---|---|---|---|
| CN | 107014975 | A | * | 8/2017 | G01N 33/24 |
| CN | 107957408 | A | * | 4/2018 | G01N 21/55 |
| CN | 112229702 | A | * | 1/2021 | G01N 3/08 |
| CN | 112924352 | A | * | 6/2021 | G01N 1/28 |
| CN | 113551956 | A | * | 10/2021 | G01N 1/28 |
| CN | 113552315 | A | * | 10/2021 | G01N 21/84 |
| CN | 115060630 | A | * | 9/2022 | G01N 15/00 |
| CN | 115078157 | A | * | 9/2022 | G01K 13/00 |
| CN | 116087055 | A | * | 5/2023 | G01N 15/08 |
| CN | 113551956 | B | * | 6/2023 | G01N 1/286 |
| CN | 117030406 | A | * | 11/2023 | G01N 1/28 |
| CN | 117192073 | A | * | 12/2023 | |
| CN | 117192137 | A | * | 12/2023 | |
| CN | 108680477 | B | * | 4/2024 | G01N 15/082 |
| EP | 1598789 | A1 | * | 11/2005 | F24F 3/16 |
| GB | 2535820 | B | * | 8/2018 | G01N 33/24 |
| JP | 4465813 | B2 | * | 5/2010 | |
| WO | WO-2020045783 | A1 | * | 3/2020 | A01G 9/246 |

* cited by examiner

AUTOMATIC TRANSPARENT SOIL PREPARATION BOX

TECHNICAL FIELD

The present application relates to the technical field of transparent soil preparation, in particular to an automatic transparent soil preparation box.

BACKGROUND

In indoor physical model tests of geotechnical engineering, the preparation of a transparent soil body is usually performed manually. The preparation of the transparent soil body requires a series of operations, and the preparation process is relatively complicated. The manual preparation method is not only time-consuming, labor-intensive and low in test efficiency, but also able to cause a situation that the soil body does not meet the test requirements due to errors in the preparation process. Therefore, the test personnel need to divert their attention from the experiment to the preparation of the soil body, which further reduces the test efficiency.

SUMMARY

In order to overcome the defects of the related art, the present application aims to provide an automatic transparent soil preparation box, so that the preparation of transparent soil is more time-saving and labor-saving, and the test efficiency is improved.

In order to solve the above problems, the technical solution adopted by the present application is as follows: an automatic transparent soil preparation box includes a box body, and a model tank carrying module, an AB liquid mixing module, a refractive index measurement module and a solid particle spreading module which are arranged in the box body. The model tank carrying module is configured to carry a model tank and transfer the model tank into and out of the box body. The AB liquid mixing module includes liquid inlet assemblies and a first stirring assembly, the liquid inlet assemblies being configured to inject A/B liquid into the model tank, and the first stirring assembly being configured to stir and mix the A/B liquid. The refractive index measurement module includes a sampling assembly and a measurement assembly, the sampling assembly being able to suck an AB mixture sample from the model tank and transfer the AB mixture sample to the measurement assembly, and the measurement assembly being configured to measure a refractive index of the AB mixture sample. The solid particle spreading module includes a spreading assembly and a second stirring assembly, the spreading assembly being configured to spread solid particles into the model tank, and the stirring assembly being configured to stir and mix the solid particles and an AB mixture.

Compared with the related art, the present application has the beneficial effects that: the model tank carrying module is able to transfer the model tank into the box body during preparation; the liquid inlet assemblies are able to inject the A/B liquid into the model tank according to the required amount of the A/B liquid, and the first stirring assembly is able to extend into the model tank to stir and mix the A/B liquid; the sampling assembly is able to suck the AB mixture sample from the model tank, and transfer the AB mixture sample to the measurement assembly, and the measurement assembly measures the refractive index of the AB mixture sample; after the refractive index of the AB mixture meets the requirements, the spreading assembly is able to spread the solid particles into the model tank according to the required amount of the solid particles, and the second stirring assembly mixes the AB mixture with the solid particles and stirs to remove foam; after the preparation of a transparent soil body is completed, the model tank carrying module transfers the model tank out of the box body, so that the staff take down the model tank with the prepared transparent soil body. Therefore, the preparation box realizes the automatic preparation of the transparent soil, which is more time-saving and labor-saving compared with manual preparation, so that the test personnel mainly focus on a test, thereby improving the test efficiency.

In the automatic transparent soil preparation box, the model tank carrying module includes a first driving piece installed in the box body and a carrying sliding table connected to an output end of the first driving piece. The box body is provided with a first slide rail, and the carrying sliding table is slidably connected to the first slide rail.

In the automatic transparent soil preparation box, the model tank carrying module further includes a second driving piece installed in the box body and a folding platform connected to an output end of the second driving piece. The folding platform is rotatably connected to the box body, the folding platform is provided with a second slide rail, and the second driving piece is able to drive the folding platform to rotate to a position where the second slide rail and the first slide rail are aligned to each other relative to the box body.

In the automatic transparent soil preparation box, two sets of liquid inlet assemblies are provided, the two sets of liquid inlet assemblies are able to respectively inject A liquid and B liquid into the model tank, and each liquid inlet assembly includes a liquid inlet pipe, a conveying pipe and a liquid outlet pipe which are sequentially connected, and further includes a magnetic pump configured to suck the liquid into the liquid inlet pipe.

In the automatic transparent soil preparation box, the conveying pipe is spiral, and the liquid outlet pipe is snakelike.

In the automatic transparent soil preparation box, the first stirring assembly and the second stirring assembly both include stirring blades. The stirring blades are able to rotate, move horizontally and move vertically relative to the box body.

In the automatic transparent soil preparation box, the sampling assembly includes a sampling tube and a sample dropping tube which are sequentially connected. The measurement assembly includes a refractometer and a refractive index measurement control panel. The sampling tube is able to extend into the model tank to suck the AB mixture sample, and drop the AB mixture sample onto a measuring slide of the refractometer through the sample dropping tube.

In the automatic transparent soil preparation box, the spreading assembly includes a feed hopper, a spreading roller brush rotatably connected below the feed hopper and a screen located below the spreading roller brush. The feed hopper is able to move horizontally and vertically relative to the box body.

In the automatic transparent soil preparation box, the spreading assembly further includes a weighing sensor and a filler scraper plate. The weighing sensor is connected to the feed hopper, the filler scraper plate is able to move horizontally and vertically relative to the feed hopper, the weighing sensor is configured to weigh the weight of the solid particles, and the filler scraper plate is configured to pre-level the solid particles.

In the automatic transparent soil preparation box, the box body includes an incubator and a storage box connected under the incubator. The model tank carrying module is able to transfer the model tank into and out of the incubator.

In the automatic transparent soil preparation box, an air conditioner and a lighting tube are installed in the incubator, a temperature and feed control panel is installed outside the incubator, the incubator is enclosed by double-layer sheet metal plates and a metal frame, and insulation cotton is filled between the double-layer sheet metal plates.

In the automatic transparent soil preparation box, an upper part of the incubator is provided with an upturning cabin door, while the periphery thereof is provided with a front side-hung cabin door, a lateral side-hung cabin door and a rear side-hung cabin door, and the front side-hung cabin door is provided with an observation window.

In the automatic transparent soil preparation box, the storage box is enclosed by a metal plate, a cooling fan is installed in the storage box, and a side wall of the storage box is provided with a main power switch.

The present application is elaborated in detail below with reference to the drawings and specific implementations.

DETAILED DESCRIPTION OF THE EMBODIMENTS

Figure 1:
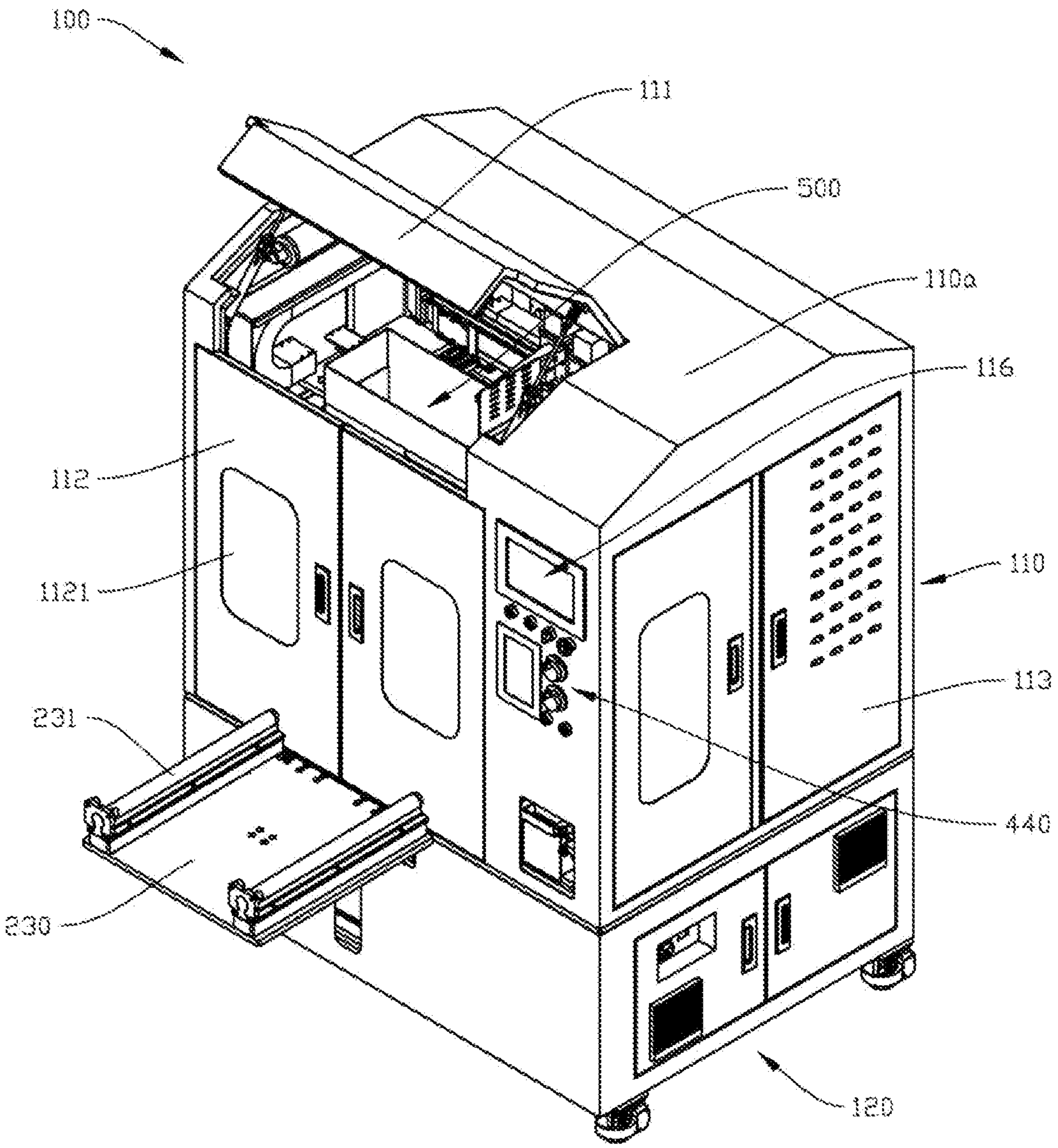
FIG. 1 is a first overall schematic structural diagram of a preparation box according to an embodiment of the present application.

An embodiment of the present application is described in detail below. Referring to FIG. 1 to FIG. 8, the embodiment of the present application provides an automatic transparent soil preparation box, which includes a box body 100, and a model tank carrying module 200, an AB liquid mixing module 300, a refractive index measurement module 400, a solid particle spreading module 500 and a main power switch 600 which are arranged in the box body 100. The model tank carrying module 200 is configured to carry a model tank 700 and transfer the model tank 700 into and out of the box body 100. The AB liquid mixing module 300 includes liquid inlet assemblies 300*a* and a first stirring assembly 300*b*, the liquid inlet assemblies 300*a* being configured to inject A/B liquid into the model tank 700, and the first stirring assembly 300*b* being configured to stir and mix the A/B liquid. The refractive index measurement module 400 includes a sampling assembly 400*a* and a measurement assembly 400*b*, the sampling assembly 400*a* being able to suck an AB mixture sample from the model tank 700 and transfer the AB mixture sample to the measurement assembly 400*b*, and the measurement assembly 400*b* being configured to measure a refractive index of the AB mixture sample. The solid particle spreading module 500 includes a spreading assembly 500*a* and a second stirring assembly 500*b*, the spreading assembly 500*a* being configured to spread solid particles into the model tank 700, and the stirring assembly 500*b* being configured to stir and mix the solid particles and an AB mixture.

Figure 2:
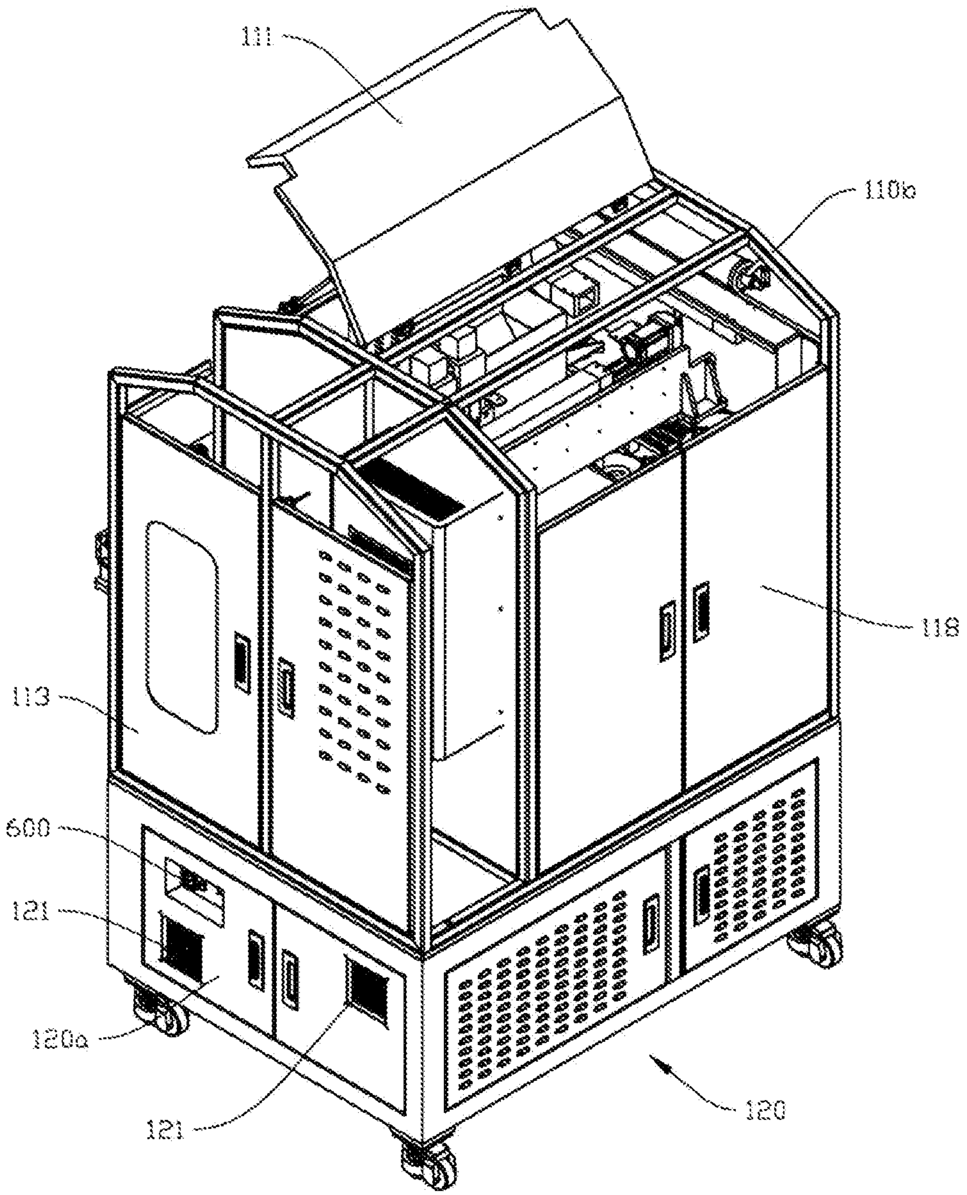
FIG. 2 is a second overall schematic structural diagram of a preparation box according to an embodiment of the present application.

Referring to FIG. 1, the box body 100 includes an incubator 110 and a storage box 120 connected under the incubator 110. The preparation process of a solid body is performed in the incubator 110, and the storage tank 120 may be configured to install driving pieces of some modules, other parts of the preparation box or other items. Specifically, the incubator 110 is enclosed by double-layer sheet metal plates 110*a* and a metal frame 110*b*, and insulation B1-level cotton is filled between the double-layer sheet metal plates 110*a*, so that the incubator 110 has a good thermal insulation effect and airtightness, and the preparation process is in a constant temperature state. As shown in FIG. 1 and FIG. 2, an upper part of the incubator 110 is provided with an upturning cabin door 111. After the upturning cabin door 111 is opened, the solid particles are put into the solid particle spreading module 500. The periphery of the incubator 110 is provided with a front side-hung cabin door 112, a lateral side-hung cabin door 113 and a rear side-hung cabin door 118. When the front side-hung cabin door 112 is opened, the model tank carrying module 200 transfers the model tank 700 into and out of the incubator 110, and the lateral side-hung cabin door 113 and the rear side-hung cabin door 118 are easily opened by the test personnel to check, repair or clean the internal structure of the incubator 110. The front side-hung cabin door 112 is provided with an observation window 1121, which facilitates the test personnel to observe the internal operation of the incubator 110 at any time. A temperature sensor, a small wall-mounted air conditioner 114, a door opening and closing sensor, a lighting tube 115 and other structures are installed in the incubator 110, and a sidewall of the incubator 110 is provided with a temperature and feed control panel 116, so that the test personnel operate at the temperature and feed control panel 116, set the internal temperature of the incubator 110, and perform door opening and closing operations. The storage box 120 is located under the incubator 110, and is enclosed by a metal plate 120*a*. A cooling fan 121 is installed in the storage box 120 to avoid the temperature in the storage box 120 from too high. A side wall of the storage box 120 is provided with the main power switch 600, and the main power switch 600 is configured to control the on-off of a power supply of the whole preparation box. A lower end of the storage box 120 is provided with multiple rollers able to facilitate the whole box body 100 to move to the appropriate position.

Figure 3:
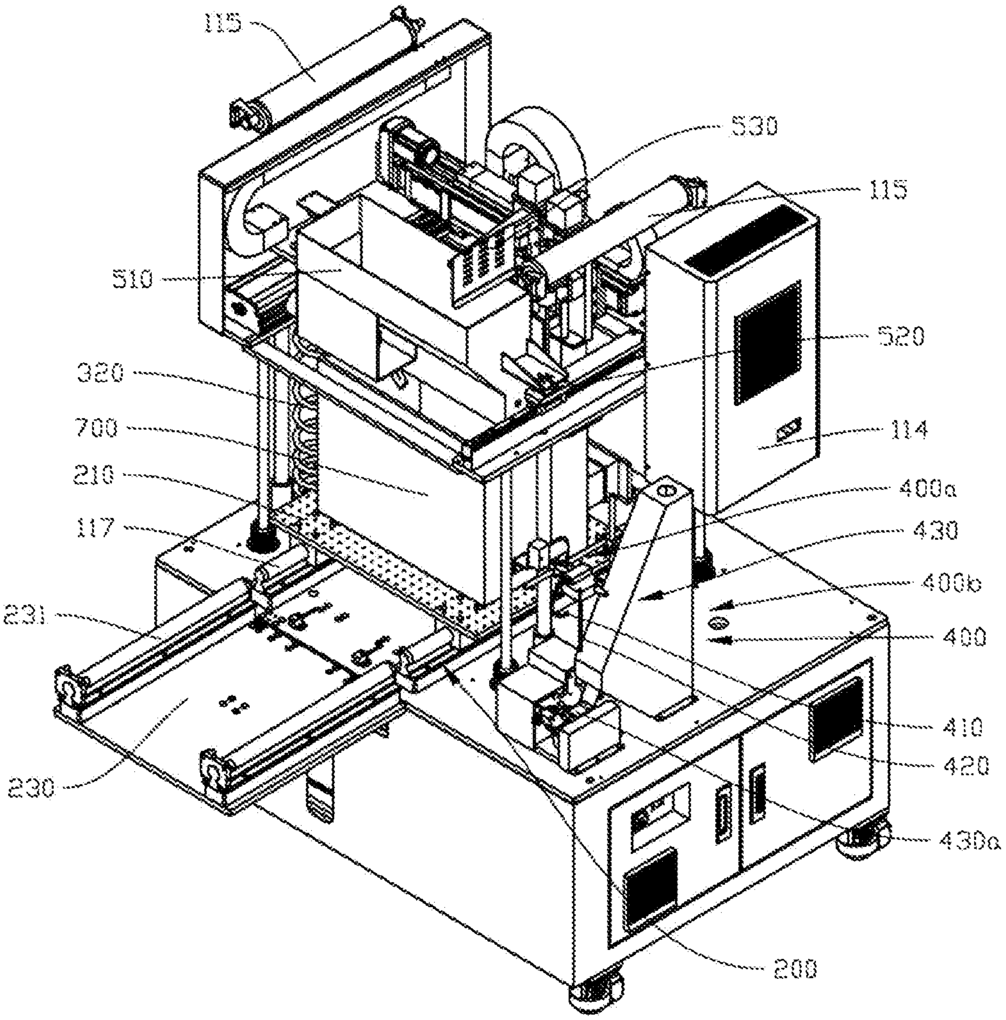
FIG. 3 is a first partial schematic structural diagram of a preparation box according to an embodiment of the present application.
Figure 4:
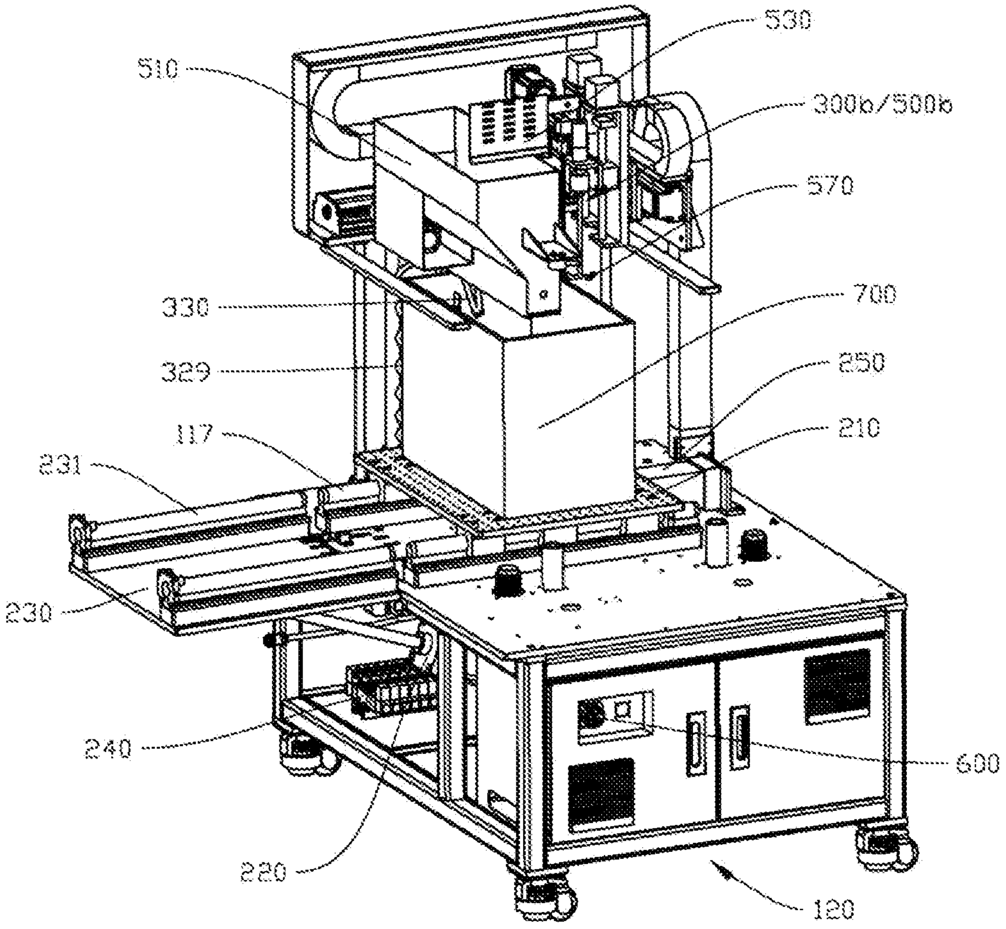
FIG. 4 is a second partial schematic structural diagram of a preparation box according to an embodiment of the present application.
Figure 5:
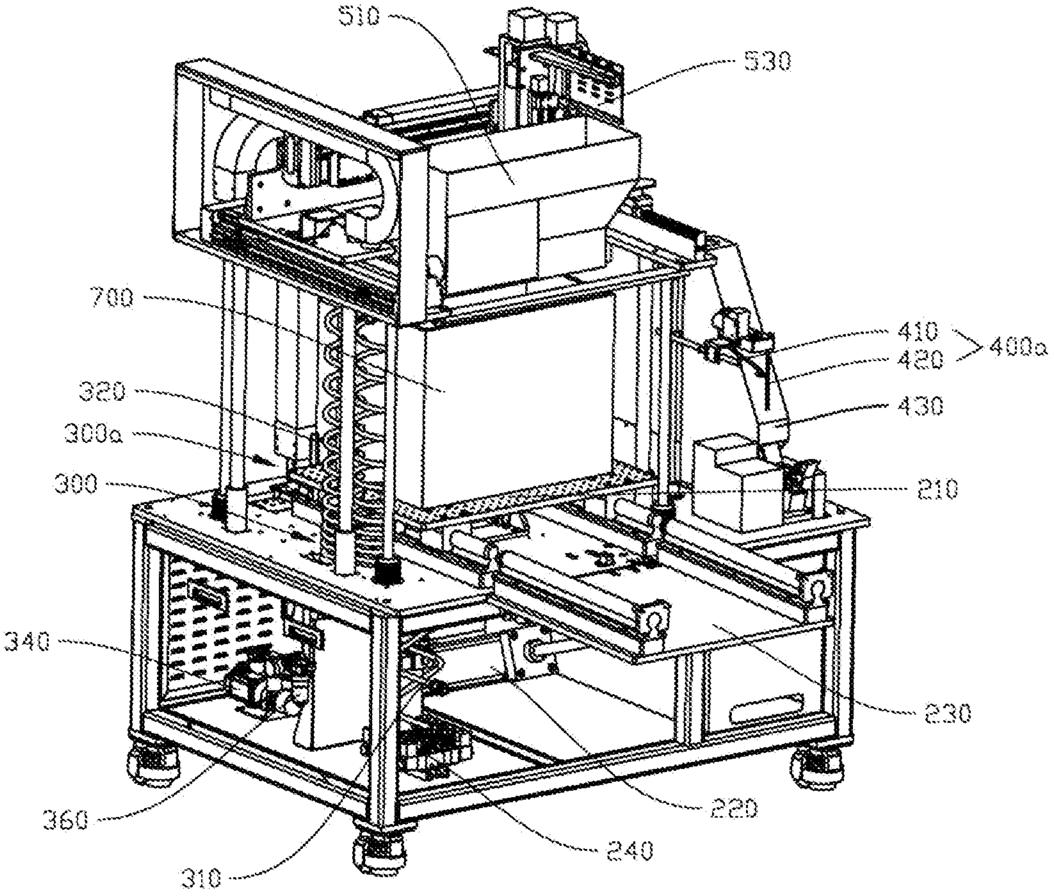
FIG. 5 is a third partial schematic structural diagram of a preparation box according to an embodiment of the present application.
Figure 6:
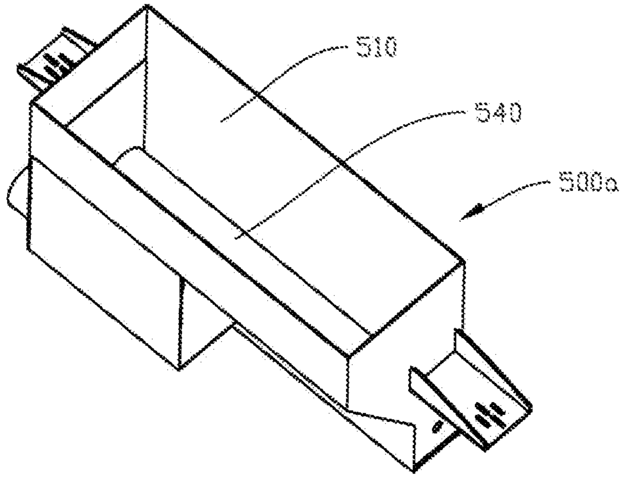
FIG. 6 is a first partial schematic structural diagram of a spreading assembly according to an embodiment of the present application.

Referring to FIG. 3 to FIG. 5, the model tank carrying module 200 includes a first driving piece 250 installed in the box body 100 and a carrying sliding table 210 connected to an output end of the first driving piece 250. The box body 100 is provided with a first slide rail 117, the carrying sliding table 210 is slidably connected to the first slide rail 117, and the carrying sliding table 210 is configured to carry the model tank 700. The first driving piece 250 is able to drive the carrying sliding table 210 to slide on the first slide rail 117 to transfer the model tank 700 into and out of the incubator 110. Further, the model tank carrying module 200 further includes a second driving piece 220 installed in the box body 100 and a folding platform 230 connected to an output end of the second driving piece 220. The folding platform 230 is rotatably connected to the box body 100, the folding platform 230 is provided with a second slide rail 231, and the second driving piece 220 is able to drive the folding platform 230 to rotate to a position where the second slide rail 231 and the first slide rail 117 are aligned to each other relative to the box body 100. When the preparation of the soil body is not required, the folding platform 230 is folded downward and attached to an outer side wall of the storage box 120. When the preparation of the soil body is required, the second driving piece 220 drives the folding platform 230 to fold upward and turn up until the folding platform 230 is placed horizontally, and the second slide rail 231 and the first slide rail 117 are aligned to each other. Through the control of instructions input by the test personnel at the temperature and feed control panel 116, the first driving piece 250 drives the carrying sliding table 210 to slide from the first slide rail 117 to the second slide rail 231, so that the carrying sliding table 210 slides outside the incubator 110, and the test personnel place the model tank 700 on the carrying sliding table 210. Then the first driving piece 250 drives the carrying sliding table 210 to transfer the model tank 700 into the incubator 110. After the preparation is completed, the first driving piece 250 drives the carrying sliding table 210 to transfer the model tank 700 out, so that the test personnel take the model tank 700 away. The second driving piece 220 drives the folding platform 230 to fold downward and retract again. Specifically, the first driving piece 250 and the second driving piece 220 are cylinders. The model tank carrying module 200 further includes electromagnetic air valve 240 and an air inlet filter. The electromagnetic valve 240 is installed in the storage box 120 and configured to control the expansion and contraction of guide rods in the cylinders. The air inlet filter is configured to filter the impurities and water vapor in the gas pumped into the cylinders to prolong the service life of the cylinder.

Figure 7:
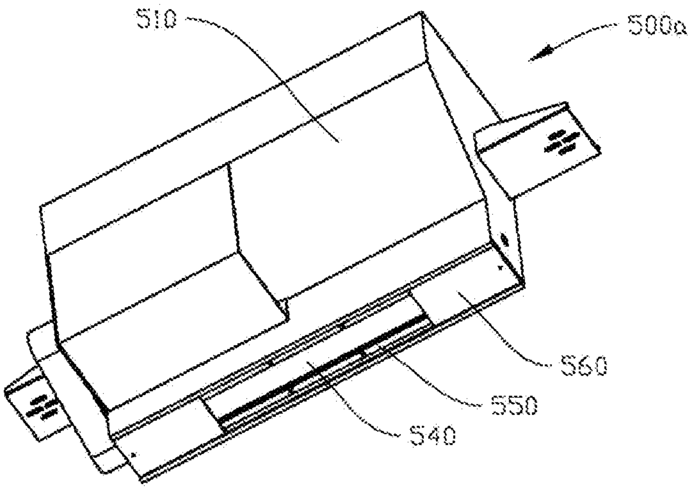
FIG. 7 is a second partial schematic structural diagram of a spreading assembly according to an embodiment of the present application.
Figure 8:
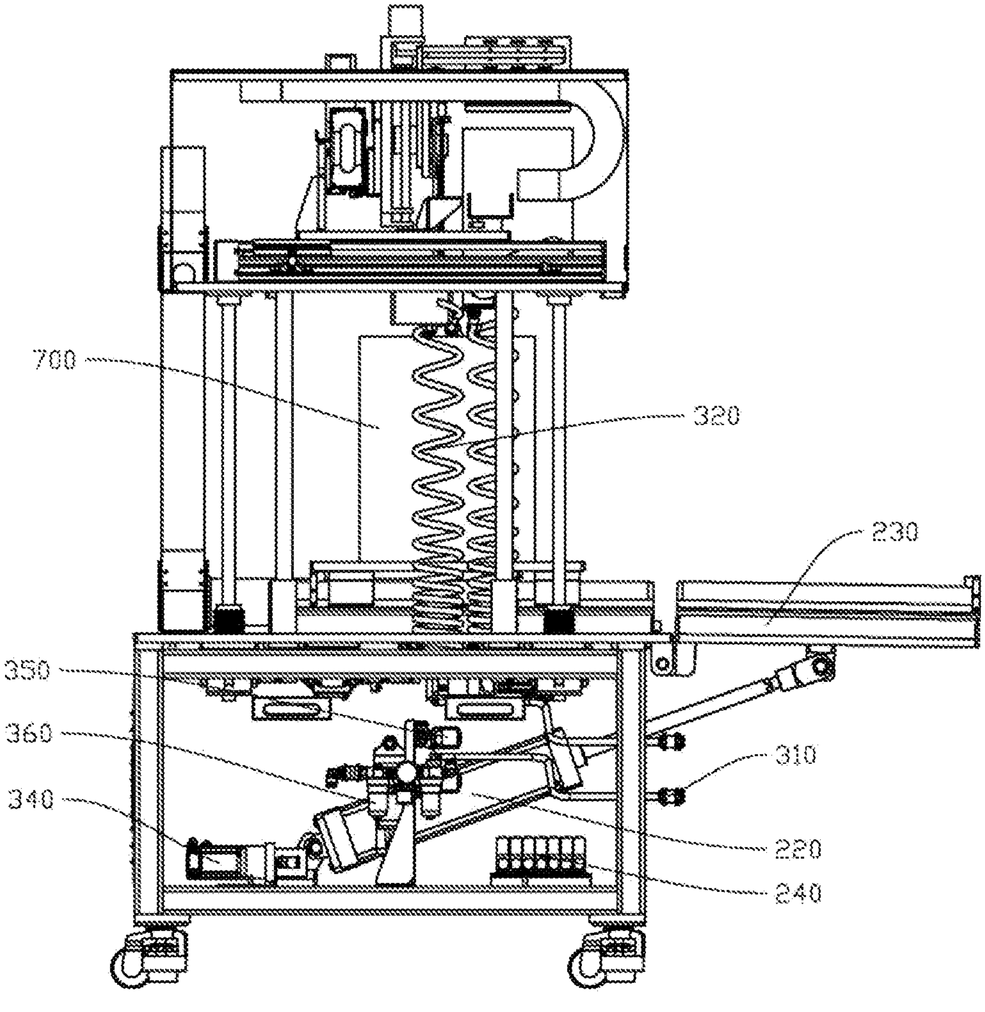
FIG. 8 is a fourth partial schematic structural diagram of a preparation box according to an embodiment of the present application.

Further, two sets of liquid inlet assemblies 300*a* are provided, and the two sets of liquid inlet assemblies 300*a* are able to respectively inject A liquid and B liquid. Referring to FIG. 3 to FIG. 5, each liquid inlet assembly 300*a* includes a liquid inlet pipe 310, a conveying pipe 320 and a liquid outlet pipe 330 which are sequentially connected. Referring to FIG. 7, each liquid inlet assembly 300*a* further includes a magnetic pump 340, a fluid on-off valve 350 and a pipeline filter 360. The liquid inlet pipe 310 is connected to a container containing the liquid A/B through a rubber tube and other pipelines. The test personnel input the instructions at the temperature and feed control panel 116 to control the input and the input amount of the A/B liquid. The magnetic pump 340 sucks the A/B liquid in the container into the liquid inlet pipe 310, and the fluid on-off valve 350 is configured to control the conveying of the A/B liquid. After passing through the liquid inlet pipe 310, the conveying pipe 320 and the liquid outlet pipe 330, the liquid flows from a pipe orifice of the pipe outlet pipe 330 into the model tank 700. The liquid inlet pipe 310, the magnetic pump 340, the fluid on-off valve 350 and the pipeline filter 360 are installed in the storage tank 120. Side walls of the storage tank 120 are provided with holes to facilitate the connection between the liquid inlet pipe 310 and an external container. The conveying pipe 320 and the liquid outlet pipe 330 are arranged in the incubator 110. The conveying pipe 320 is spiral, the liquid outlet pipe 330 is snakelike, and the position of the liquid outlet pipe 330 is adjustable to facilitate the insertion into the model tank 700 to provide the liquid A/B. In some embodiments, the first stirring assembly 300*b* and the second stirring assembly 500*b* share a set of assemblies, including the stirring blades 570. As shown in FIG. 3, the stirring blades 570 rotate, move horizontally and move vertically relative to the box body 100 to facilitate mixing and stirring throughout the model tank 700, so that the mixture is fully stirred and mixed. Specifically, a motor, a slide rail and other structures are used to drive the stirring blades 570 to move horizontally and vertically relative to the box body 100, so as to adjust the position of the stirring blades 570. The motor is used to drive the stirring blades 570 to stir rotatably.

Referring to FIG. 3, FIG. 4 and FIG. 5, the sampling assembly 400*a* includes a sampling tube 410 and a sample dropping tube 420 which are sequentially connected. The measurement assembly 400*b* includes a refractometer 430 and a refractive index measurement control panel 440. The sampling tube 410 is able to extend into the model tank 700 to suck the AB mixture sample, and drop the AB mixture sample onto a measuring slide 430*a* of the refractometer 430 through the sample dropping tube 420. The refractive index measurement control panel 440 is installed outside the incubator 110, and is provided with a refractive index liquid crystal display screen, a field of view focusing button, a light and shade boundary adjusting button, a titration button and a light inlet prism opening and closing button, etc. so as to facilitate the test personnel to complete the measurement of the refractive index. The refractometer 430 is an Abbe refractometer 430, which is configured to measure the refractive index of the AB mixture, and the measuring range is 1.3000 to 1.7000.

Referring to FIG. 3 to FIG. 7, the spreading assembly 500*a* includes a feed hopper 510, a weighting sensor 520 connected to the feed hopper 510, a filler scraper plate 530 located above the feed hopper 510, a spreading roller brush 540 rotatably connected to a discharge port under the feed hopper 510 and a screen 550 located below the spreading roller brush 540. After opening the upturning cabin door 111, the solid particles are put into the feed hopper 510, the weighing sensor 520 is configured to weigh the solid particles, and the filler scraper plate 530 is able to move horizontally and vertically relative to the feed hopper 510 and is configured to pre-level the solid particles. The feed hopper 510 is able to move horizontally and vertically relative to the box body 100 to adjust the spreading position of the feed hopper 510. When the spreading roller brush 540 rotates, the solid particles fall from the discharge port to the model tank 700 through the screen 550, so that the spreading is more uniform. Specifically, the movement of the feed hopper 510 is realized by a servo motor, the slide rail and other structures, which will not be elaborated herein. Further, the spreading assembly 500*a* further includes a replaceable spreading fixed width plate 560. The replaceable spreading fixed width plate 560 is installed at the bottom of the feed hopper 510 and located below the spreading roller brush 540, and the length and width of a spreading outlet are adjusted according to the size of the model tank 700.

During the preparation, the preparation box moves to the appropriate position for the test, the rollers at the lower end of the storage box 120 are locked, the power supply is connected, and the main power switch 600 is turned on. Operations are performed on the temperature and feed control panel 116, the folding platform 230 is unfolded, and the upturning cabin door 111 and the front side-hung cabin door 112 are opened. The first driving piece 250 transfers the carrying sliding table 210 to the folding platform 230, the test personnel place the model tank 700 on the carrying sliding table 210, and then the first driving piece 250 transfers the carrying sliding table 210 and the model tank 700 back to the incubator 110. The width of the spreading fixed width plate 560 is adjusted according to the width of the model tank 700, the transparent sand particles with required weight are loaded into the hopper, and the soil material is scraped using the scraper plate. Joints of the external liquid inlet pipe 310 of the A/B liquid on the metal plate 120*a* at a front side of the lower storage box 120 are respectively connected to a container of A/B mineral oil, the liquid outlet pipe 330 of the A/B liquid extends into the model tank 700, and the upturning cabin door 111 and the front side-hung cabin door 112 of the incubator 110 are closed. The temperature in the incubator 110 on the temperature and feed control panel 116 is set. The temperature is consistent with the subsequent test temperature. The refractive index of a mixture to be prepared is provided on the refractive index adjustment control panel, the calculated corresponding proportions of liquid A and B are sucked, the refractive index of the mixture is measured after stirring the mixture is uniformly stirred by the stirring blades 570, and fine adjustment is performed according to a target refractive index until the test requirements are met. The spreading speed, a movement path of the feed hopper 510, etc. are provided on the temperature and feed control panel 116. The spreading roller brush 540 rotates for spreading. After spreading at the single layer ends, the stirring blades 570 extend into the model tank 700, stirring and foam removing are performed according to the set speed, a stirring path, the number of single-layer stirring cycles, etc. and then spreading at the next layer is performed until spreading is fully completed. After the preparation of the transparent soil body is completed, the front side-hung cabin door 112 of the incubator 110 is opened, the carrying sliding table 210 is removed, the model tank 700 moves into a specific pre-consolidation instrument for pre-consolidation, and then the model test is performed. After the preparation of the solid body is completed and the model tank 700 is removed, the main power switch 600 is turned off, a device in the incubator 110 is cleaned, a connection between the external liquid inlet pipe 310 of the A/B liquid and the container of the A/B liquid is disconnected, the folding platform 230 is folded to be in front of a front side panel of the lower storage tank 120, and the preparation box moves to the original position. The preparation box integrates liquid mixing, refractive index measurement, solid particle spreading, etc. into the preparation box. During the preparation, the model tank 700 and the solid particle spreading module 500 are located in the incubator 110, so that the preparation process is in a constant temperature state. The preparation process is basically fully automated, and is more time-saving and labor-saving compared with manual preparation, so that the test personnel mainly focus on a test, thereby improving the test efficiency.

It is to be noted that, in the description of the present application, any references to the orientation descriptions, such as the orientations or positional relationships indicated by upper, down, front, rear, left, right, etc. are based on the orientations or positional relationships shown in the drawings, and are only for the convenience of describing the present application and simplifying the description. The description does not indicate or imply that the apparatus or element referred to must have a specific orientation, be constructed and operated in a specific orientation, and therefore cannot be construed as limiting the present application.

In the description of the present application, several means one or more, multiple means two or more than two, greater than, less than, more than, etc. are understood to not include the given number, while above, below, within, etc. are understood to include the given number. If first, second, etc. are described, they are used for descriptive purposes only, and cannot be understood as indicating or implying relative importance or implicitly indicating the number of indicated technical features or implicitly indicating the precedence relationship of the indicated technical features.

In the description of the present application, unless otherwise defined, set, install, connect, etc. should be broadly understood. The specific meaning of the above-mentioned words in the present application may be reasonably determined by those skilled in the art in conjunction with the specific content of the technical solution.

The above-mentioned implementations are only the preferred implementations of the present application, and are not intended to limit the scope of protection of the present application, and any non-substantial change and replacement made by those skilled in the art based on the present application belong to the scope of protection of the present application.

What is claimed is:

1. An automatic transparent soil preparation box, comprising a box body, and a model tank carrying module, an A and B liquid mixing module, a refractive index measurement module and a solid particle spreading module which are arranged in the box body; wherein

- the model tank carrying module is configured to carry a model tank and transfer the model tank into and out of the box body;
- the A and B liquid mixing module comprises liquid inlet assemblies and a first stirring assembly, the liquid inlet assemblies are configured to inject A and B liquids into the model tank, and the first stirring assembly is configured to stir and mix the A and B liquids to form an AB mixture;
- the refractive index measurement module comprises a sampling assembly and a measurement assembly, the sampling assembly is able to suck a sample of the AB mixture from the model tank and transfer the sample of the AB mixture to the measurement assembly, and the measurement assembly is configured to measure a refractive index of the sample of the AB mixture; and
- the solid particle spreading module comprises a spreading assembly and a second stirring assembly, the spreading assembly is configured to spread solid particles into the model tank, and the second stirring assembly is configured to stir and mix the solid particles and the AB mixture.

2. The automatic transparent soil preparation box according to claim 1, wherein the model tank carrying module comprises a first driving piece installed in the box body and a carrying sliding table connected to an output end of the first driving piece, the box body is provided with a first slide rail, and the carrying sliding table is slidably connected to the first slide rail.

3. The automatic transparent soil preparation box according to claim 2, wherein the model tank carrying module further comprises a second driving piece installed in the box body and a folding platform connected to an output end of the second driving piece, the folding platform is rotatably connected to the box body, the folding platform is provided with a second slide rail, and the second driving piece is able to drive the folding platform to rotate to a position where the second slide rail and the first slide rail are aligned to each other relative to the box body.

4. The automatic transparent soil preparation box according to claim 1, wherein two sets of liquid inlet assemblies are provided, the two sets of liquid inlet assemblies are able to respectively inject A liquid and B liquid into the model tank, and each liquid inlet assembly comprises a liquid inlet pipe, a conveying pipe and a liquid outlet pipe which are sequentially connected, and further comprises a magnetic pump configured to suck the liquid into the liquid inlet pipe.

5. The automatic transparent soil preparation box according to claim 4, wherein the conveying pipe is spiral, and the liquid outlet pipe is snakelike.

6. The automatic transparent soil preparation box according to claim 1, wherein the first stirring assembly and the second stirring assembly both comprise stirring blades, the stirring blades are able to rotate, move horizontally and move vertically relative to the box body.

7. The automatic transparent soil preparation box according to claim 1, wherein the sampling assembly comprises a sampling tube and a sample dropping tube which are sequentially connected, and the measurement assembly comprises a refractometer and a refractive index measurement control panel, the sampling tube is able to extend into the model tank to suck the sample of the AB mixture, and drop the sample of the AB mixture onto a measuring slide of the refractometer through the sample dropping tube.

8. The automatic transparent soil preparation box according to claim 1, wherein the spreading assembly comprises a feed hopper, a spreading roller brush rotatably connected below the feed hopper and a screen located below the spreading roller brush, the feed hopper is able to move horizontally and vertically relative to the box body.

9. The automatic transparent soil preparation box according to claim 8, wherein the spreading assembly further comprises a weighing sensor and a filler scraper plate, the weighing sensor is connected to the feed hopper, the filler scraper plate is able to move horizontally and vertically relative to the feed hopper, the weighing sensor is configured to weigh the weight of the solid particles, and the filler scraper plate is configured to pre-level the solid particles.

10. The automatic transparent soil preparation box according to claim 1, wherein the box body comprises an incubator and a storage box connected under the incubator, the model tank carrying module is able to transfer the model tank into and out of the incubator.

11. The automatic transparent soil preparation box according to claim 10, wherein an air conditioner and a lighting tube are installed in the incubator, a temperature and feed control panel is installed outside the incubator, the incubator is enclosed by double-layer sheet metal plates and a metal frame, and insulation cotton is filled between the double-layer sheet metal plates.

12. The automatic transparent soil preparation box according to claim 10, wherein an upper part of the incubator is provided with an upturning cabin door, while the periphery thereof is provided with a front side-hung cabin door, a lateral side-hung cabin door and a rear side-hung cabin door, and the front side-hung cabin door is provided with an observation window.

13. The automatic transparent soil preparation box according to claim 10, wherein the storage box is enclosed by a metal plate, a cooling fan is installed in the storage box, and a side wall of the storage box is provided with a main power switch.

* * * * *